United States Patent [19]
Podell et al.

[11] Patent Number: 4,575,476
[45] Date of Patent: Mar. 11, 1986

[54] DIPPED RUBBER ARTICLE

[75] Inventors: Howard I. Podell, 28 Beachfront La., New Rochelle, N.Y. 10805; Albert Goldstein, Tinton Falls, N.J.; David C. Blackley, Chesham, England; Michael H. James, Harpenden, England; David M. Bratby; Roger Duck, both of London, England

[73] Assignee: Howard I. Podell, New Rochelle, N.Y.

[21] Appl. No.: 555,805

[22] Filed: Nov. 28, 1983

Related U.S. Application Data

[63] Continuation-in-part of Ser. No. 445,436, Nov. 30, 1982, Pat. No. 4,499,154, and Ser. No. 216,889, Dec. 16, 1980, Pat. No. 4,482,577.

[30] Foreign Application Priority Data

Sep. 3, 1982 [GB] United Kingdom ............... 8225200

[51] Int. Cl.$^4$ .............................................. A41D 19/00
[52] U.S. Cl. ..................... 428/494; 428/521; 2/167; 2/168; 2/DIG. 7; 128/132 R; 427/133
[58] Field of Search ...................... 428/494, 515, 521; 2/167, 168, DIG. 7; 128/132 R

[56] References Cited

U.S. PATENT DOCUMENTS

| | | | |
|---|---|---|---|
| 2,621,333 | 12/1952 | Thomas et al. | 2/168 |
| 3,411,892 | 11/1968 | Kavalir et al. | 428/494 X |
| 3,728,739 | 4/1973 | Semp | 2/168 |
| 3,745,042 | 7/1973 | Tim et al. | 427/384 X |
| 3,813,695 | 6/1974 | Podell, Jr. et al. | 2/168 |
| 3,856,561 | 12/1974 | Esemplare et al. | 428/494 |
| 3,872,515 | 3/1975 | Miner et al. | 2/168 |
| 3,919,442 | 11/1975 | Esemplare et al. | 428/494 |
| 3,959,554 | 5/1976 | Hick | 428/336 |
| 4,064,564 | 12/1977 | Casey | 2/168 |
| 4,082,862 | 4/1978 | Esemplare et al. | 428/494 X |
| 4,100,309 | 7/1979 | Micklus et al. | 427/2 |
| 4,143,109 | 3/1979 | Stockum | 264/112 |
| 4,302,852 | 12/1981 | Joung | 2/167 |
| 4,304,008 | 12/1981 | Joung | 2/167 |
| 4,310,928 | 1/1982 | Joung | 2/168 X |

FOREIGN PATENT DOCUMENTS

| | | |
|---|---|---|
| 1434453 | 3/1965 | France . |
| 1453817 | 8/1966 | France . |
| 2193710 | 7/1972 | France . |
| 2297910 | 1/1976 | France . |

Primary Examiner—George F. Lesmes
Assistant Examiner—Nancy A. B. Swisher
Attorney, Agent, or Firm—Darby & Darby

[57] ABSTRACT

A skin-contacting lubricating layer formed from a hydrogel polymer bonded to a rubber article (such as a surgeon's glove) is treated by means of surfactant material (such as a bactericidal cationic surfactant which preferably has a 6–18C alkyl or alkenyl group, such as an N-hexadecyl group) or a long chain fatty amine so as to substantially improve the lubricity of the layer with respect to damp skin.

The hydrogel polymer is preferably a copolymer of 2-hydroxyethylmethacrylate (HEMA) with methacrylic acid (MAA) or with 2-ethylhexyl acrylate (EHA) or with both MAA and EHA. Such a hydrogel polymer has improved lubricity to dry skin and, if used for this purpose, need not be treated with a surfactant or fatty amine to improve the lubricity with respect to damp skin.

13 Claims, 1 Drawing Figure

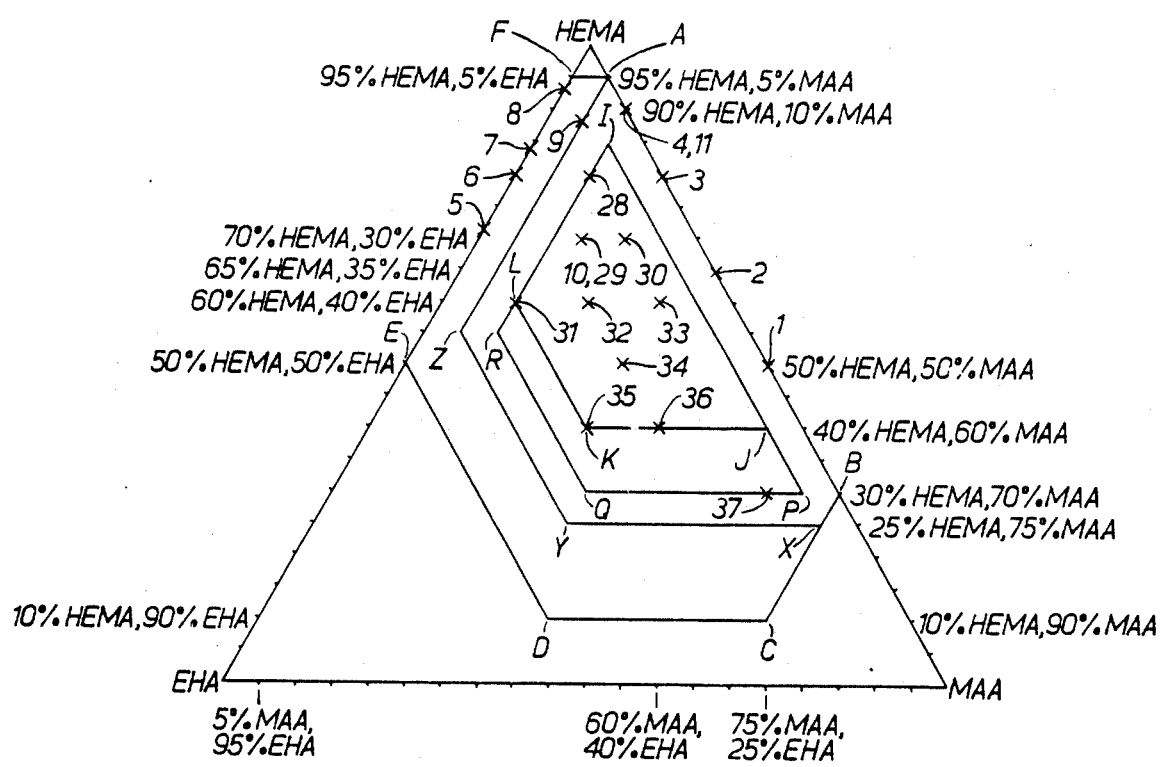

4,575,476

DIPPED RUBBER ARTICLE

This application is a continuation-in-part of copending application Ser. No. 445,436, now U.S. Pat. No. 4,499,154 and of copending application Ser. No. 216,889, filed Dec. 16, 1980, now U.S. Pat. No. 4,482,577.

The present invention is concerned with flexible rubber articles and, in particular, thin-walled rubber gloves of the kind used by surgeons.

Surgeon's gloves are difficult to don and to facilitate donning a powdered lubricant, such as particulate epichlorhydrin-treated maize starch, is conventionally applied to the inner surface of the gloves. There is a risk of such powdered lubricant escaping from the interior of the glove to contaminate the surgical field, the lubricant escaping either during donning or, as sometimes happens, if the glove is punctured during an operation.

Proposals have been made for polymeric lubricant coatings which are bonded to the inner surface of such gloves and which, because they are bonded, cannot escape from the glove.

Examples of such proposals are in U.S. Pat. Nos. 4,070,713 and 4,143,109, which disclose gloves which have an inner layer of elastomeric material with particulate lubricant embedded therein, and U.S. Pat. Nos. 3,813,695, 3,856,561 and 4,302,852, which disclose surgeon's gloves with various polymeric slip coatings bonded to the inner surface thereof.

U.S. Pat. No. 3,813,695 ("the Podell patent") describes a surgeon's glove in which the glove material is formed of a laminate consisting of an outer layer of flexible material, for example rubber, and an inner layer of hydrophilic plastic material (such as a hydrogel polymer), the inner and outer layers being bonded together.

There are many known hydrogel polymers, examples of which are polyvinyl pyrrolidone, polyhydroxyethyl acrylate or methacrylate, polyhydroxypropyl acrylate or methacrylate, and copolymers of these with each other or with acrylic or methacrylic acid, acrylic or methacrylic esters or vinyl pyridine.

There are many disclosures of the coating of rubber articles, such as catheters and bathing caps, with such hydrogel polymers by dipping in a solution of a hydrophilic, hydrogel-forming polymer and curing the resulting polymer layer.

Examples of such disclosures include U.S. Pat. Nos. 3,326,742, 3,585,103, 3,607,473, 3,745,042, 3,901,755, 3,925,138, 2,930,076, 3,940,533, 3,966,530, 4,024,317, 4,110,495 and 4,125,477, and British Pat. Nos. 1028446 and 859297.

We have evaluated many such hydrogel polymers and have surprisingly found that certain 2-hydroxyethyl methacrylate polymers provide superior lubricity with respect to dry skin and can be appropriately treated to provide superior lubricity with respect to damp skin.

According to the present invention, therefore, there is provided a flexible rubber article having bonded thereto a layer providing a skin-contacting surface of the article, said layer being formed from a hydrogel polymer comprising a copolymer of a 2-hydroxyethyl methacrylate (HEMA) with methacrylic acid (MAA) or with 2-ethylhexyl acrylate (EHA), or a ternary copolymer of HEMA, MAA and EHA, said copolymer having a composition within the bounds of the area ABCDEF in the attached ternary composition diagram. The area ABCDEF is believed to cover substantially all of the hydrogel-forming area of the composition diagram, apart from HEMA homopolymer and HEMA copolymers with up to 5% EHA and/or MAA.

The composition is preferably within area ABXYZ, more preferably within area PQRI. It is most preferred that the composition is within area IJKL.

In some embodiments, such a copolymer may contain HEMA and MAA in a molar ratio of at least 1:1 (such as 1 to 10:1) or HEMA and EHA in a molar ratio of at least 2.5:1 (such as 2.5 to 10:1).

The copolymer, which is preferably prepared by solution polymerisation (bulk polymerisation is less satisfactory), may be a binary copolymer of HEMA and MAA or EHA, or it may be a ternary copolymer of these monomers with EHA; a preferred such terpolymer has a monomer molar ratio of HEMA to (MAA+EHA) of 67:33 to 90:10 (that is 2 to 9:1) and a molar ratio of EHA to (HEMA+MAA) of 5:97 to 20:80 (that is 1: about 20 to 4).

Minor amounts of further monomers which do not impair the properties of the copolymer may be used in addition. A mixture of such copolymers can be employed, either with other such copolymers or with minor amounts of other polymers which do not impair the properties of the hydrogel-forming polymer.

It is to be noted that the EHA is of a hydrophobic nature and assists in the bonding of the hydrogel polymer to the (hydrophobic) rubber substrate. EHA also serves as a plasticizer and increases the flexibility of the layer formed from the hydrogel polymer (which is bonded to a flexible rubber substrate). EHA may accordingly be replaced by an alkyl acrylate or methacrylate which acts in a corresponding manner.

The MAA serves to furnish cross-linking sites in the copolymer; the methyl group in MAA may influence the copolymer by (i) modifying the reactivity of the carboxyl groups and thus influencing the rate and degree of cross-linking, and (ii) by modifying the rate at which MAA is incorporated into the polymer backbone and hence the distribution of cross-linking sites along the polymer chain.

Copolymers as described above provide better lubricity with respect to dry skin than any other hydrogel-forming polymer of the many we have evaluated; there is, however, a great difference between lubricity relative to dry skin and relative to damp skin. Since surgeons prefer to don their gloves after "scrubbing up", without fully driving their hands, their hands are distinctly damp. We have found that most hydrogel polymers used as bonded inner layers in surgeons' gloves, as suggested in the Podell patent, give totally inadequate lubricity as regards damp hands.

The layer formed from the hydrogel polymer according to the invention is preferably cross-linked. Such cross-linking generally lowers the water-absorption of the polymer. After cross-linking, the layer may be surface treated with a physiologically acceptable surfactant or long chain fatty amine; this can enhance the lubricity of the layer with respect to damp skin.

Such surfactants and fatty amines improve the lubricity with respect to damp skin for a wide range of hydrogel polymers as well as the specific 2-hydroxyethyl methacrylate copolymers referred to above. According to another aspect of the invention, therefore, there is provided a flexible rubber article having a layer formed from a hydrogel polymer bonded thereto to provide a skin-contacting surface of the article, in which the layer is surface treated with a surfactant or a long chain fatty amine, which is preferably bactericidal or bacteriostatic. The surfactant used is preferably ionic (it may sometimes be preferred for the surfactant to have opposite polarity to that of the hydrogel-forming polymer); cationic surfactants are particularly preferred. Such cationic surfactants may have a free anion, such as a halide ion, or the anion may be part of the molecular structure of the surfactant (that is, the latter has a betaine structure).

Preferred cationic surfactants are quaternary ammonium compounds having at least one 6–18C hydrocarbyl (alkenyl or alkyl) group; a preferred hydrocarbyl group is a hexadecyl group. It is further preferred that the hydrocarbyl group is attached to a quaternary nitrogen atom which is part of a heterocyclic ring (such as a pyridine, morpholine or imidazoline ring).

Most preferred cationic surfactants are hexadecyl trimethyl ammonium chloride, N-lauryl pyridinium chloride, N-cetyl pyridinium chloride, the corresponding bromides, or a hydroxyethyl heptadecenyl imidazoline salt, all of which significantly improve the lubricity with respect to damp skin without adversely affecting lubricity with respect to dry skin.

Non-ionic and anionic surfactants may be used instead of cationic surfactants; examples of suitable non-ionic surfactants include ethylene oxide condensates (such as polyethylene oxide, ethylene oxide-polypropylene glycol condensates, and polyglycol-polyamine condensates). An example of a suitable anionic surfactant is sodium lauryl sulphate.

When a (neutral) fatty amine is used, this preferably has a 6–18C hydrocarbyl group (such as a hexadecyl group) attached to the nitrogen atom. A preferred such amine is N,N-dimethyl hexadecylamine (which is commercially available as Armeen 16D).

The use of cationic surfactants serves to inhibit bacterial growth when the layer formed from the hydrogel polymer is in contact with the skin; this is an advantage for surgeon's gloves because, as mentioned above, these are sometimes punctured during surgical procedures, and any bacteria which have grown on the surgeon's skin since commencement of the operation may be released into the surgical field.

The surfactant or fatty amine is generally used in the form of a solution, such as an aqueous solution (typically an aqueous solution containing at least 0.2% by weight, up to, for example, 2% by weight) of a cationic surfactant as just mentioned.

The article according to the invention is preferably treated with a silicone liquid so as to reduce the surface tack on any surfaces not coated with a layer formed from the hydrogel polymer; this treatment is preferably carried out at the same time as treatment with a surfactant as mentioned above. It is preferred that treatment with a silicone (such as medical grade polydimethyl siloxane) is carried out with a bath containing at least 0.05% by weight of silicone (for example, 0.05 to 0.4% by weight).

The rubber used in the article according to the present invention may be a natural or synthetic rubber; natural rubber is preferred. It is also preferred that the article according to the invention should be formed (prior to bonding of the layer formed from hydrogel polymer thereto) by dipping of a rubber latex. The hydrogel layer is preferably applied to the rubber before vulcanisation thereof; this has the surprising result that the skin-contacting surface has a much cooler feel. This may be because there is greater vapour transmission through the final coated article.

According to another aspect of the invention therefore, there is provided a dipped rubber article having bonded thereto a lubricating layer providing a skin-contacting surface of said article, the lubricating layer being formed by applying a solution of a hydrophilic hydrogel-forming polymer to said dipped article prior to complete vulcanisation thereof, and curing the polymer and vulcanising the rubber.

The lubricating layer is perspiration-absorbent and enables powdered lubricants to be dispensed with.

The hydrogel-forming polymer solution, which preferably contains a curing agent therefor, is preferably applied by dipping the rubber article in the solution.

An article according to the invention can be produced by a process comprising the steps of:

(a) forming a rubber article by dipping a former in a rubber latex,
(b) leaching the rubber article in hot water,
(c) priming the rubber surface of the article on the former, for example, by means of a dilute acid,
(d) rinsing the primed surface in water or aqueous alkali,
(e) dipping said article, while still on the former, in a solution of a hydrophilic, hydrogel-forming polymer and a curing agent therefor,
(f) heat drying the resulting coating such that the resulting hydrogel polymer is bonded to said rubber,
(g) vulcanising the rubber and simultaneously curing the polymer by application of heat,
(h) stripping the resulting article from the former,
(i) applying a solution of surfactant material containing silicone to the article (for example, by tumbling in such a solution), optionally after washing, and
(j) heating the resulting coating of surfactant material so as to fix the slip properties of the coating.

Our tests have shown that, following step (j), the damp skin slip properties and the dry skin slip properties of the coating formed from the hydrogel polymer are advantageously not impaired by subsequent washing (that is, surfactant material is not leached out to any substantial extent on washing of the coated article).

The application of the solution of surfactant material provides a substantially tack-free outer surface (that is, the surface not coated with hydrogel polymer), in addition to the inner surface, which is, of course, advantageous.

The rubber surface to which the hydrogel polymer is bonded may also be primed by dipping in, for example, a solution of an aluminium salt after priming with dilute acid.

It is a feature of the present invention that the production of the dipped rubber article, leaching, priming, application of hydrogel polymer layer, and vulcanisation of the rubber and curing of the polymer can all be carried out in a continuous operation.

The present invention has been described primarily, with reference to surgeons' gloves; it is, however, applicable to other skin- or tissue-contacting flexible rubber articles, such as condoms, gloves used by doctors and veterinary surgeons for examination purposes (such gloves being often donned with dry hands), catheters, urethers, sheets and sheath-type incontinence devices.

When the present invention is used for aricles such as urethers and catheters, the layer formed from hydrogel polymer is provided on the outer surface (this being the skin-contacting surface); for condoms the layer formed from hydrogel polymer may be provided on the inner surface and/or on the outer surface.

In order that the present invention may be more fully understood, the following Examples and Comparative Examples are given by way of illustration only.

EXAMPLE 1

A thin dipped surgeons glove of natural rubber latex was leached with sulphuric acid, rinsed, primed by dipping in aluminium sulphate solution, dried out completely and then dipped into a 4% alcoholic solution of a copolymer of 2-hydroxyethyl methacrylate (HEMA) and methacrylic acid (MAA) in a 1:1 molar ratio, followed by drying. The solution contained, in addition to the copolymer, 5 parts per hundred of partially methylated melamine-formaldehyde resin (as cross-linking agent) and 0.5 parts per hundred of paratoluene sulphonic acid (as catalyst).

The rubber was then vulcanised, after which the lubricity with respect to dry skin was subjectively evaluated on a scale of 1 to 5, in which:

1 means that the film is sticky
2 means that poor slip is obtained
3 means that moderate slip is obtained
4 means that quite good slip is obtained
5 means that excellent slip is obtained (comparable to the use of a powdered surface).

The dry skin lubricity number was 5; the coating adhered satisfactorily to the rubber and no visible flaking was observed.

EXAMPLES 2 TO 11

Example 1 was repeated, except that the copolymer was replaced by the polymers indicated in the following Table 1:

TABLE 1

| Example No. | Polymer | Molar ratio of monomers | Dry skin lubricity number |
|---|---|---|---|
| 2 | HEMA/MAA | 2:1 | 5 |
| 3 | HEMA/MAA | 5:1 | 5 |
| 4 | HEMA/MAA | 10:1 | 5 |
| 5 | HEMA/EHA | 2.5:1 | 5 |
| 6 | HEMA/EHA | 4:1 | 5 |
| 7 | HEMA/EHA | 5:1 | 5 |
| 8 | HEMA/EHA | 10:1 | 5 |
| 9 | HEMA/MAA/EHA | 10:1:0.5 | 5 |
| 10 | HEMA/MAA/EHA | 5:1:1.2 | 5 |
| 11 | HEMA/MAA/BA | 10:1:0.5 | 5 |
| Comparative 1 | HEMA/AA | 2:1 | 4 |
| Comparative 2 | HEMA/AA | 1:1 | 4 |
| Comparative 3 | HEMA/MMA | 2:1 | 4 |
| Comparative 4 | HEMA/MMA | 1:1 | 4 |
| Comparative 5 | HEMA/BA | 5:1 | 4 |
| Comparative 6 | HEMA/BA | 2:1 | 3 |
| Comparative 7 | HEMA/MA | 2:1 | 4 |
| Comparative 8 | HEMA/IA | 2:1 | 4 |
| Comparative 9 | HEMA/EHA | 2:1 | 4 |
| Comparative 10 | HEMA/EHA | 1:1 | 4 |
| Comparative 11 | MMA/VPd | 1:1 | 3 |
| Comparative 12 | HEMA | — | 3-4 |
| Comparative 13 | HEA | — | 3-4 |
| Comparative 14 | VPd | — | 2 |
| Comparative 15 | HPMA | — | 3-4 |
| Comparative 16 | HEMA/HEA | 1:1 | 4 |
| Comparative 17 | HEMA/VPd | 1:1 | 3-4 |
| Comparative 18 | HEMA/HPMA | 1:1 | 4 |
| Comparative 19 | HEA/HPMA | 1:1 | 4 |
| Comparative 20 | HEMA/VPy | 9:1 | 4-5 |

In the above Table, the abbreviations have the following meanings:

EHA: 2-ethylhexyl acrylate
BA: butyl acrylate
AA: acrylic acid
MMA: methyl methacrylate
MA: methyl acrylate
IA: itaconic acid
VPd: N-vinyl pyrrolidone
HEA: hydroxyethyl acrylate
HPMA: hydroxypropyl methacrylate
VPy: vinyl pyridine (quaternised)

It will be seen that the dry skin lubricity for each of the Examples according to the invention was better than that obtained in any of the Comparative Examples (the only comparative sample approaching the lubricity of the samples according to the invention was that of Comparative Example 20, when a quaternised copolymer was used).

In each of the Examples according to the invention, the coating adhered satisfactorily with at most very slight flaking. This also applied to the Comparative Examples, except Comparative Example 14 (where the coating was washed off on wet-stripping).

The dry frictional force and the coefficient of friction for the glove of Example 6, the glove of Example 10 and for a conventional powdered glove are given in the following Table 2.

TABLE 2

| Glove | Dry frictional force | Coefficient of friction |
|---|---|---|
| Example 6 | 48.7 g | 0.20 |
| Example 10 | 53.1 g | 0.218 |
| Conventional powdered | 78.5 g | 0.323 |

The damp skin lubricity number was 2 for Examples 1 to 11 and Comparative Examples 2 to 10, 12, 13, and 15 to 20, and 1 for Comparative Examples 1, 11 and 14.

EXAMPLES 12 TO 21

Samples prepared as in Example 10 were posttreated by dipping in solutions of various materials, as identified in the following Table 3.

TABLE 3

| Example No. | Material | Concentration of solution | Damp skin lubricity number |
|---|---|---|---|
| 12 | N—cetylpyridinium chloride (N—CPC) | 5% | 3-4 |
| 13 | N—cetylpyridinium chloride (N—CPC) | 1% | 3-4 |
| 14 | sodium lauryl sulphate | 5% | 3 |
| 15 | sodium lauryl sulphate | 1.0% | 3 |
| 16 | sodium lauryl sulphate | 0.5% | 3 |
| 17 | sodium lauryl sulphate | 0.1% | 2-3 |
| 18 | N,N—dimethyl hexadecylamine | 1% | 3-4 |
| 19 | Ethylene oxide-polypropylene glycol condensate | 1% | 3 |
| 20 | Distearyl dimethyl ammonium chloride | 1% | 3 |
| 21 | Hexadecyl trimethyl ammonium chloride | 1% | 3-4 |

In each case, the dry slip was substantially unimpaired.

EXAMPLES 22 TO 26

Example 12 was repeated, using solutions containing various proportions of N-CPC and also 0.3% medical grade polydimethyl siloxane, as indicated in the following Table 4.

TABLE 4

| Example No. | Percentage N—CPC | Damp skin lubricity number |
|---|---|---|
| 22 | 0.1 | 3 |
| 23 | 0.25 | 3–4 |
| 24 | 0.50 | 4 |
| 25 | 1.0 | 4 |
| 26 | 2.0 | 4 |

Similar results to those of Example 22 were obtained when the percentage of polydimethyl siloxane was 0.05%

EXAMPLE 27

A series of hand-shaped formers were dipped into a natural rubber latex to produce a thin rubber layer on each former. The rubber layer was leached in hot water and then primed by dipping in dilute sulphuric acid, rinsed, dipped into a caustic soda bath of pH 10.5 containing hydrogen peroxide in an amount sufficient to react with hydrogen sulphide formed in the priming stage. The rubber, still on the formers, was then dipped into a 4% ethanolic solution of a HEMA/MAA/EHA terpolymer with a monomer molar ratio of 5:1:1.2, the solution also containing 5 to 15 parts per hundred (based on the weight of polymer) of partially methylated melamine-formaldehyde resin available commercially as Cymel 373 (as cross-linking agent) and 0.5 to 1.5 parts per hundred (on the same basis) of para-toluene sulphonic acid (as catalyst).

The rubber was then vulcanised and the polymer simultaneously cured (the temperature being raised from 80° to 150° C. over 25 minutes during vulcanisation), the resulting gloves being stripped from the formers.

The stripped gloves were washed with water and then tumbled in an aqueous solution containing 0.75% by weight of N-cetylpyridinium chloride, the solution also containing 0.05% by weight of emulsified silicone. The gloves were finally tumbled dry at 65° C. for 75 minutes.

The resulting gloves had a dry skin lubricity number of 5 and a wet skin lubricity number of 4 on their polymer-coated surfaces (used as the insides of the gloves).

No allergenic or irritant reaction to the gloves was reported, even when the gloves were worn by surgeons with hypersensitive skin.

EXAMPLE 28

Example 1 was repeated except that the copolymer was replaced by a copolymer having the following molar percentage: 80% HEMA, 10% MAA, 10% EHA. A dry skin lubricity number of 5 was obtained.

EXAMPLE 29

A rubber-coated porcelain mandrel was dipped for several minutes in water at above 70° C., rinsed in running water, and dipped in 2% sulphuric acid at 40° C. The coated mandrel was then dipped for (neutralisation) in dilute caustic (pH 9–10) and then dipped in water wash tanks at 40° C. The coated mandrel was then coated with a 10% solution in ethanol of a terpolymer as used in Example 10, the solution containing 10% by weight of Cymel 370 (cross-linking agent) and 1% by weight of p-toluenesulphonic acid.

The coated mandrel was heated in an oven for 30 minutes with temperatures rising to 105° C.

The glove was stripped from the mandrel and immersed for 15 minutes in an aqueous dispersion of 0.05% of 35% Silicone medical grade emulsion DC365 (Dow Corning brand) containing 0.5% Cetylpyridinium chloride. After draining, the glove was heated and dried in an oven for 30 minutes at 70° C.

The outer surface of the glove was tack-free; the inner coated surface was hydrophilic, had a high degree of slip and was readily donned on a dry hand (a dry skin lubricity number of 5).

The moisture transmission properties at 25° C. (100% RH) of the resulting glove and an otherwise similar, but uncoated (control), glove are set out in the following Table 5.

TABLE 5

| Sample | Rate of moisture transmission ($gm/m^2/mm/24$ hrs.) |
|---|---|
| According to the invention | 7.86 |
| Control | 4.22 |

EXAMPLES 30 TO 37

Example 1 was repeated, except that the copolymer was replaced by the polymers indicated in the following Table 6.

TABLE 6

| Example No. | Molar percentage HEMA | Molar percentage MAA | Molar percentage EHA |
|---|---|---|---|
| 30 | 70 | 20 | 10 |
| 31 | 60 | 10 | 30 |
| 32 | 60 | 20 | 20 |
| 33 | 60 | 30 | 10 |
| 34 | 50 | 30 | 20 |
| 35 | 40 | 30 | 30 |
| 36 | 40 | 40 | 20 |
| 37 | 30 | 60 | 10 |

In each case, a dry skin lubricity number of 5 was obtained.

EXAMPLES 38 TO 53

Example 12 was repeated, using solutions of various surfactants instead of N-CPC. The results are summarised in the following Table 7.

EXAMPLE 54

Example 1 was repeated, except that the copolymer was replaced by a copolymer having the following molar percentage: 70% HEMA, 10% MAA, 10% EHA. A dry skin lubricity number of 5 was obtained.

TABLE 7

| Example No. | Surfactant | Concentration of solution | Damp skin lubricity number |
|---|---|---|---|
| 38 | Octadecyl trimethyl-ammonium bromide | 1.0% | 3 |
| 39 | Cetyl pyridinium bromide | 1.0% | 3–4 |

TABLE 7-continued

| Example No. | Surfactant | Concentration of solution | Damp skin lubricity number |
|---|---|---|---|
| 40 | 2-oleyl-1-(ethylbetaoxy propionic acid) imidazoline | 1.0% | 3 |
| 41 | Lauryl pyridinium chloride | 1.0% | 3-4 |
| 42 | Oxyethyl alkyl ammonium phosphate | 1.0% | 3 |
| 43 | 10-18 C alkyl dimethyl benzyl ammonium chloride | 1.0% | 3 |
| 44 | Polypropoxy quaternary ammonium acetate | 1.0% | 3 |
| 45 | 12-14 C alkylbetaine | 1.0% | 3 |
| 46 | Coconut imidazoline betaine | 1.0% | 3 |
| 47 | An amine oxide ethoxylate (Empigen DY) | 1.0% | 3 |
| 48 | N—cetyl-N—ethyl morpholinium ethosulphate | 1.0% | 3 |
| 49 | Distearyl dimethylammonium chloride | 1.0% | 3 |
| 50 | Pluronic F38 (an ethylene oxide-polypropylene glycol of mol. wt. 5020) | 0.15% | 3 |
| 51 | Polyethylene oxide (mol. wt. 400000) | 1.0% | 3 |
| 52 | Dodecylbenzyl-hydroxymethyl dimethyl chloride | 1.0% | 3 |
| 53 | Cetyl stearyl ethylene oxide condensate (20 ethylene oxide units). | 5% | 3 |

We claim:

1. A flexible rubber article having a lubricating layer formed from a hydrogel polymer bonded thereto so as to provide a skin-contacting surface of said article in which a member of the group consisting of surfactant materials and long chain fatty amines has been applied to said skin-contacting surface so as to substantially improve the lubricity of said surface with respect to damp skin, said hydrogel polymer being a copolymer of 2-hydroxyethyl methacrylate with at least one of methacrylic acid and 2-ethylhexyl acrylate.

2. An article according to claim 1, in which the surfactant material comprises an ionic surfactant.

3. An article according to claim 2, in which said surfactant is cationic.

4. An article according to claim 3, in which said surfactant is a quaternary ammonium compound having at least one 6-18 C hydrocarbyl group.

5. An article according to claim 4, in which said hydrocarbyl group is attached to a quaternary nitrogen atom which is part of a heterocyclic ring.

6. An article according to claim 5, in which the heterocyclic ring is pyridine, morpholine or imidazoline.

7. An article according to claim 6, in which the surfactant is an N-lauryl or N-cetyl pyridinium salt, or a hydroxyethyl heptadecenyl imidazoline salt.

8. An article according to claim 4, in which said surfactant is hexadecyl trimethyl ammonium chloride.

9. An article according to any one of claims 1 and 2-8 in which the copolymer has a composition within from 25 to 95% 2-hydroxyethylmethacrylate, from 5 to 75% methacrylic acid and from zero to 40% 2-ethylhexylacrylate.

10. An article according to claim 1, said copolymer having a composition within from zero to 50% 2-ethylhexylacrylate, from zero to 70% methacrylic acid and from 10 to 95% 2-hydroxyethylmethacrylate.

11. An article according to claim 10, said copolymer having a composition within from 5 to 35% 2-ethylhexylacrylate, from 15 to 70% methacrylic acid and from 30 to 85% 2-hydroxyethyl methacrylate.

12. An article according to claim 1, the lubricating layer having been formed by applying a solution of said polymer to said article prior to complete vulcanization thereof and curing the polymer and vulcanizing the rubber.

13. An article according to claim 12, in which said solution is applied by dipping.

* * * * *